United States Patent
Friddle et al.

(12)

(10) Patent No.: US 6,900,045 B2
(45) Date of Patent: May 31, 2005

(54) HUMAN KINASE PROTEINS AND POLYNUCLEOTIDES ENCODING THE SAME

(75) Inventors: Carl Johan Friddle, The Woodlands, TX (US); Erin Hilbun, Houston, TX (US); Boris Nepomnichy, Houston, TX (US); Yi Hu, Spring, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/940,921

(22) Filed: Aug. 28, 2001

(65) Prior Publication Data

US 2002/0147320 A1 Oct. 10, 2002

Related U.S. Application Data

(60) Provisional application No. 60/229,280, filed on Aug. 31, 2000.

(51) Int. Cl.$^7$ .......................... C12N 1/20; C12N 15/00; C12N 5/00; C12Q 1/68; C07H 21/04
(52) U.S. Cl. ....................... 435/252.3; 536/23.2; 435/6; 435/320.1; 435/325; 435/194
(58) Field of Search ........................ 536/23.2; 435/194, 435/252.3, 320.1, 6, 325

Primary Examiner—Maryam Monshipouri

(57) ABSTRACT

Novel human polynucleotide and polypeptide sequences are disclosed that can be used in therapeutic, diagnostic, and pharmacogenomic applications.

7 Claims, No Drawings

SEQUENCE LISTING

<160> NUMBER OF SEQ ID NOS: 10

<210> SEQ ID NO 1
<211> LENGTH: 2052
<212> TYPE: DNA
<213> ORGANISM: homo sapiens

<400> SEQUENCE: 1

| | | | | | |
|---|---|---|---|---|---|
| atggataagt | acgatgtgat | taaggccatc | gggcaaggtg | ccttcgggaa | agcatactta | 60 |
| gctaaaggga | aatcagatag | caagcactgt | gtcataaaag | agatcaattt | tgaaaagatg | 120 |
| cccatacaag | aaaaagaagc | ttcaaagaaa | gaagtgattc | ttctggaaaa | gatgaaacat | 180 |
| cccaacattg | tagccttctt | caattcattt | caagagaatg | gcaggctgtt | tattgtaatg | 240 |
| gaatattgtg | atggagggga | tctcatgaaa | aggatcaata | gacaacgggg | tgtgttattt | 300 |
| agtgaagatc | agatcctcgg | ttggtttgta | cagatttctc | taggactaaa | acatattcat | 360 |
| gacaggaaga | tattacacag | ggacataaaa | gctcagaaca | ttttcttag | caagaacgga | 420 |
| atggtggcaa | agcttgggga | ctttggtata | gcaagagtcc | tgaataattc | catggaactt | 480 |
| gctcgaactt | gtattggaac | accttactac | ctgtccccag | agatctgtca | gaataaaccc | 540 |
| tacaacaata | aaacggatat | tggtctctct | ggctgtgtct | tatatgagct | ctgcacactt | 600 |
| aaacatcctt | ttgagggtaa | caacttacag | cagctggttc | tgaagatttg | tcaagcacat | 660 |
| tttgccccaa | tatctccggg | gttttctcgt | gagctccatt | ccttgatatc | tcagctcttt | 720 |
| caagtatctc | ctcgagaccg | accatccata | aattccattt | tgaaaaggcc | cttttagag | 780 |
| aatcttattc | ccaaatattt | gactcctgag | gtcattcagg | aagaattcag | tcacatgctt | 840 |
| atatgcagag | caggagcgcc | agcttctcga | catgctggga | aggtggtcca | gaagtgtaaa | 900 |
| atacaaaaag | tgagattcca | gggaaagtgc | ccaccaagat | caaggatatc | tgtgccaatt | 960 |
| aaaaggaatg | ctatattgca | tagaaatgaa | tggagaccac | cagctggagc | ccagaaggcc | 1020 |
| agatctataa | aaatgataga | aagacccaaa | attgctgctg | tctgtggaca | ttatgattat | 1080 |
| tattatgctc | aacttgatat | gctgaggagg | agagcccaca | aaccaagtta | tcaccctatt | 1140 |
| cctcaagaaa | atactggagt | tgaggattac | ggtcaggaaa | cgaggcatgg | tccatcccca | 1200 |
| agtcaatggc | ctgctgagta | ccttcagaga | aaatttgaag | ctcaacaata | taagttgaaa | 1260 |
| gtggagaagc | aattgggtct | tcgtccatct | tctgccgagc | caaattacaa | ccagagacaa | 1320 |
| gagctaagaa | gtaatggaga | agagcctaga | ttccaggagc | tgccatttag | gaaaaacgaa | 1380 |
| atgaaggaac | aggaatattg | gaagcagtta | gaggaaatac | gccaacagta | ccacaatgac | 1440 |
| atgaaagaaa | ttagaaagaa | gatggggaga | gaaccagagg | agaactcaaa | aataagtcat | 1500 |
| aaaacctatt | tggtgaagaa | gagtaacctg | cctgtccatc | aagatgcatc | tgagggagaa | 1560 |
| gcacctgtgc | aggacattga | aaaagacttg | aaacaaatga | ggcttcagaa | cacaaaggaa | 1620 |
| agtaaaaatc | cagaacagaa | atataaagct | aagaaggggg | taaaatttga | aattaattta | 1680 |
| gacaaatgta | tttctgatga | aaacatcctc | caagaggaag | aggcaatgga | tataccaaat | 1740 |
| gaaactttga | cctttgagga | tggcatgaag | tttaaggaat | atgaatgtgt | aaaggagcat | 1800 |
| ggagattata | cagacaaagc | atttgaaaaa | cttcactgcc | agaagcagg | gttttccacg | 1860 |
| cagactgtag | ctgctgtggg | aaacaggagg | cagtgggatg | gaggagcgcc | tcagactctg | 1920 |
| ctgcagatga | tggcagtggc | cgacatcacc | tccacctgcc | ccacggggcc | tgacagtgag | 1980 |

-continued

```
tctgtgctta gcgtcagtcg tcaggaaggg aagaccaagg acccgtacag cccagtgctc   2040
atcctgatgt ga                                                       2052
```

<210> SEQ ID NO 2
<211> LENGTH: 683
<212> TYPE: PRT
<213> ORGANISM: homo sapiens

<400> SEQUENCE: 2

```
Met Asp Lys Tyr Asp Val Ile Lys Ala Ile Gly Gln Gly Ala Phe Gly
 1               5                  10                  15

Lys Ala Tyr Leu Ala Lys Gly Lys Ser Asp Ser Lys His Cys Val Ile
                20                  25                  30

Lys Glu Ile Asn Phe Glu Lys Met Pro Ile Gln Glu Lys Glu Ala Ser
            35                  40                  45

Lys Lys Glu Val Ile Leu Leu Glu Lys Met Lys His Pro Asn Ile Val
        50                  55                  60

Ala Phe Phe Asn Ser Phe Gln Glu Asn Gly Arg Leu Phe Ile Val Met
 65                  70                  75                  80

Glu Tyr Cys Asp Gly Gly Asp Leu Met Lys Arg Ile Asn Arg Gln Arg
                85                  90                  95

Gly Val Leu Phe Ser Glu Asp Gln Ile Leu Gly Trp Phe Val Gln Ile
               100                 105                 110

Ser Leu Gly Leu Lys His Ile His Asp Arg Lys Ile Leu His Arg Asp
           115                 120                 125

Ile Lys Ala Gln Asn Ile Phe Leu Ser Lys Asn Gly Met Val Ala Lys
       130                 135                 140

Leu Gly Asp Phe Gly Ile Ala Arg Val Leu Asn Asn Ser Met Glu Leu
145                 150                 155                 160

Ala Arg Thr Cys Ile Gly Thr Pro Tyr Tyr Leu Ser Pro Glu Ile Cys
                165                 170                 175

Gln Asn Lys Pro Tyr Asn Asn Lys Thr Asp Ile Trp Ser Leu Gly Cys
            180                 185                 190

Val Leu Tyr Glu Leu Cys Thr Leu Lys His Pro Phe Glu Gly Asn Asn
        195                 200                 205

Leu Gln Gln Leu Val Leu Lys Ile Cys Gln Ala His Phe Ala Pro Ile
    210                 215                 220

Ser Pro Gly Phe Ser Arg Glu Leu His Ser Leu Ile Ser Gln Leu Phe
225                 230                 235                 240

Gln Val Ser Pro Arg Asp Arg Pro Ser Ile Asn Ser Ile Leu Lys Arg
                245                 250                 255

Pro Phe Leu Glu Asn Leu Ile Pro Lys Tyr Leu Thr Pro Glu Val Ile
            260                 265                 270

Gln Glu Glu Phe Ser His Met Leu Ile Cys Arg Ala Gly Ala Pro Ala
        275                 280                 285

Ser Arg His Ala Gly Lys Val Val Gln Lys Cys Lys Ile Gln Lys Val
    290                 295                 300

Arg Phe Gln Gly Lys Cys Pro Pro Arg Ser Arg Ile Ser Val Pro Ile
305                 310                 315                 320

Lys Arg Asn Ala Ile Leu His Arg Asn Glu Trp Arg Pro Pro Ala Gly
                325                 330                 335

Ala Gln Lys Ala Arg Ser Ile Lys Met Ile Glu Arg Pro Lys Ile Ala
            340                 345                 350
```

```
Ala Val Cys Gly His Tyr Asp Tyr Tyr Ala Gln Leu Asp Met Leu
            355                 360                 365

Arg Arg Arg Ala His Lys Pro Ser Tyr His Pro Ile Pro Gln Glu Asn
        370                 375                 380

Thr Gly Val Glu Asp Tyr Gly Gln Glu Thr Arg His Gly Pro Ser Pro
385                 390                 395                 400

Ser Gln Trp Pro Ala Glu Tyr Leu Gln Arg Lys Phe Glu Ala Gln Gln
                405                 410                 415

Tyr Lys Leu Lys Val Glu Lys Gln Leu Gly Leu Arg Pro Ser Ser Ala
            420                 425                 430

Glu Pro Asn Tyr Asn Gln Arg Gln Glu Leu Arg Ser Asn Gly Glu Glu
        435                 440                 445

Pro Arg Phe Gln Glu Leu Pro Phe Arg Lys Asn Glu Met Lys Glu Gln
    450                 455                 460

Glu Tyr Trp Lys Gln Leu Glu Glu Ile Arg Gln Gln Tyr His Asn Asp
465                 470                 475                 480

Met Lys Glu Ile Arg Lys Lys Met Gly Arg Glu Pro Glu Glu Asn Ser
                485                 490                 495

Lys Ile Ser His Lys Thr Tyr Leu Val Lys Lys Ser Asn Leu Pro Val
            500                 505                 510

His Gln Asp Ala Ser Glu Gly Glu Ala Pro Val Gln Asp Ile Glu Lys
        515                 520                 525

Asp Leu Lys Gln Met Arg Leu Gln Asn Thr Lys Glu Ser Lys Asn Pro
    530                 535                 540

Glu Gln Lys Tyr Lys Ala Lys Lys Gly Val Lys Phe Glu Ile Asn Leu
545                 550                 555                 560

Asp Lys Cys Ile Ser Asp Glu Asn Ile Leu Gln Glu Glu Glu Ala Met
                565                 570                 575

Asp Ile Pro Asn Glu Thr Leu Thr Phe Glu Asp Gly Met Lys Phe Lys
            580                 585                 590

Glu Tyr Glu Cys Val Lys Glu His Gly Asp Tyr Thr Asp Lys Ala Phe
        595                 600                 605

Glu Lys Leu His Cys Pro Glu Ala Gly Phe Ser Thr Gln Thr Val Ala
    610                 615                 620

Ala Val Gly Asn Arg Arg Gln Trp Asp Gly Gly Ala Pro Gln Thr Leu
625                 630                 635                 640

Leu Gln Met Met Ala Val Ala Asp Ile Thr Ser Thr Cys Pro Thr Gly
                645                 650                 655

Pro Asp Ser Glu Ser Val Leu Ser Val Ser Arg Gln Glu Gly Lys Thr
            660                 665                 670

Lys Asp Pro Tyr Ser Pro Val Leu Ile Leu Met
        675                 680

<210> SEQ ID NO 3
<211> LENGTH: 1965
<212> TYPE: DNA
<213> ORGANISM: homo sapiens

<400> SEQUENCE: 3
atggataagt acgatgtgat taaggccatc gggcaaggtg ccttcgggaa agcatactta    60
gctaaaggga atcagatag caagcactgt gtcataaaag agatcaattt tgaaagatg    120 cccatacaag aaaagaagc ttcaaagaaa gaagtgattc ttctggaaaa gatgaaacat    180
cccaacattg tagccttctt caattcattt caagagaatg caggctgtt tattgtaatg    240
```

```
gaatattgtg atggagggga tctcatgaaa aggatcaata gacaacgggg tgtgttattt      300
agtgaagatc agatcctcgg ttggtttgta cagatttctc taggactaaa acatattcat      360
gacaggaaga tattacacag ggacataaaa gctcagaaca ttttcttag caagaacgga       420
atggtggcaa agcttgggga ctttggtata gcaagagtcc tgaataattc catggaactt      480
gctcgaactt gtattggaac accttactac ctgtccccag atctgtca gaataaaccc        540
tacaacaata aaacggatat ttggtctctt ggctgtgtct tatatgagct ctgcacactt      600
aaacatcctt tgagggtaa caacttacag cagctggttc tgaagatttg tcaagcacat       660
tttgccccaa tatctccggg gttttctcgt gagctccatt ccttgatatc tcagctcttt      720
caagtatctc ctcgagaccg accatccata aattccattt tgaaaaggcc cttttagag      780
aatcttattc ccaaatattt gactcctgag gtcattcagg aagaattcag tcacatgctt      840
atatgcagag caggagcgcc agcttctcga catgctggga aggtggtcca gaagtgtaaa     900
atacaaaaag tgagattcca gggaaagtgc ccaccaagat caaggatatc tgtgccaatt      960
aaaggaatg ctatattgca tagaaatgaa tggagaccac cagctggagc ccagaaggcc      1020
agatctataa aaatgataga aagacccaaa attgctgctg tctgtggaca ttatgattat     1080
tattatgctc aacttgatat gctgaggagg agagcccaca accaagtta tcaccctatt      1140
cctcaagaaa atactggagt tgaggattac ggtcaggaaa cgaggcatgg tccatcccca     1200
agtcaatggc ctgctgagta ccttcagaga aaatttgaag ctcaacaata taagttgaaa     1260
gtggagaagc aattgggtct tcgtccatct tctgccgagc caaattacaa ccagagacaa     1320
gagctaagaa gtaatggaga agagcctaga ttccaggagc tgccatttag gaaaaacgaa     1380
atgaaggaac aggagaactc aaaaataagt cataaaacct atttggtgaa gaagagtaac     1440
ctgcctgtcc atcaagatgc atctgaggga gaagcacctg tgcaggacat tgaaaaagac     1500
ttgaaacaaa tgaggcttca gaacacaaag gaaagtaaaa atccagaaca gaaatataaa     1560
gctaagaagg gggtaaaatt tgaaattaat ttagacaaat gtatttctga tgaaaacatc     1620
ctccaagagg aagaggcaat ggatatacca aatgaaactt tgacctttga ggatggcatg     1680
aagtttaagg aatatgaatg tgtaaaggag catggagatt atacagacaa agcatttgaa     1740
aaacttcact gcccagaagc agggttttcc acgcagactg tagctgctgt gggaaacagg     1800
aggcagtggg atggaggagc gcctcagact ctgctgcaga tgatggcagt ggccgacatc     1860
acctccacct gccccacggg gcctgacagt gagtctgtgc ttagcgtcag tcgtcaggaa     1920
gggaagacca aggacccgta cagcccagtg ctcatcctga tgtga                     1965
```

<210> SEQ ID NO 4
<211> LENGTH: 654
<212> TYPE: PRT
<213> ORGANISM: homo sapiens

<400> SEQUENCE: 4

```
Met Asp Lys Tyr Asp Val Ile Lys Ala Ile Gly Gln Gly Ala Phe Gly
 1               5                  10                  15

Lys Ala Tyr Leu Ala Lys Gly Lys Ser Asp Ser Lys His Cys Val Ile
                20                  25                  30

Lys Glu Ile Asn Phe Glu Lys Met Pro Ile Gln Glu Lys Glu Ala Ser
            35                  40                  45

Lys Lys Glu Val Ile Leu Leu Glu Lys Met Lys His Pro Asn Ile Val
        50                  55                  60
```

-continued

```
Ala Phe Phe Asn Ser Phe Gln Glu Asn Gly Arg Leu Phe Ile Val Met
 65                  70                  75                  80

Glu Tyr Cys Asp Gly Asp Leu Met Lys Arg Ile Asn Arg Gln Arg
                 85                  90                  95

Gly Val Leu Phe Ser Glu Asp Gln Ile Leu Gly Trp Phe Val Gln Ile
                100                 105                 110

Ser Leu Gly Leu Lys His Ile His Asp Arg Lys Ile Leu His Arg Asp
                115                 120                 125

Ile Lys Ala Gln Asn Ile Phe Leu Ser Lys Asn Gly Met Val Ala Lys
    130                 135                 140

Leu Gly Asp Phe Gly Ile Ala Arg Val Leu Asn Asn Ser Met Glu Leu
145                 150                 155                 160

Ala Arg Thr Cys Ile Gly Thr Pro Tyr Tyr Leu Ser Pro Glu Ile Cys
                165                 170                 175

Gln Asn Lys Pro Tyr Asn Asn Lys Thr Asp Ile Trp Ser Leu Gly Cys
                180                 185                 190

Val Leu Tyr Glu Leu Cys Thr Leu Lys His Pro Phe Glu Gly Asn Asn
                195                 200                 205

Leu Gln Gln Leu Val Leu Lys Ile Cys Gln Ala His Phe Ala Pro Ile
    210                 215                 220

Ser Pro Gly Phe Ser Arg Glu Leu His Ser Leu Ile Ser Gln Leu Phe
225                 230                 235                 240

Gln Val Ser Pro Arg Asp Arg Pro Ser Ile Asn Ser Ile Leu Lys Arg
                245                 250                 255

Pro Phe Leu Glu Asn Leu Ile Pro Lys Tyr Leu Thr Pro Glu Val Ile
                260                 265                 270

Gln Glu Glu Phe Ser His Met Leu Ile Cys Arg Ala Gly Ala Pro Ala
                275                 280                 285

Ser Arg His Ala Gly Lys Val Val Gln Lys Cys Lys Ile Gln Lys Val
    290                 295                 300

Arg Phe Gln Gly Lys Cys Pro Pro Arg Ser Arg Ile Ser Val Pro Ile
305                 310                 315                 320

Lys Arg Asn Ala Ile Leu His Arg Asn Glu Trp Arg Pro Pro Ala Gly
                325                 330                 335

Ala Gln Lys Ala Arg Ser Ile Lys Met Ile Glu Arg Pro Lys Ile Ala
                340                 345                 350

Ala Val Cys Gly His Tyr Asp Tyr Tyr Ala Gln Leu Asp Met Leu
                355                 360                 365

Arg Arg Arg Ala His Lys Pro Ser Tyr His Pro Ile Pro Gln Glu Asn
    370                 375                 380

Thr Gly Val Glu Asp Tyr Gly Gln Glu Thr Arg His Gly Pro Ser Pro
385                 390                 395                 400

Ser Gln Trp Pro Ala Glu Tyr Leu Gln Arg Lys Phe Glu Ala Gln Gln
                405                 410                 415

Tyr Lys Leu Lys Val Glu Lys Gln Leu Gly Leu Arg Pro Ser Ser Ala
                420                 425                 430

Glu Pro Asn Tyr Asn Gln Arg Gln Glu Leu Arg Ser Asn Gly Glu Glu
                435                 440                 445

Pro Arg Phe Gln Glu Leu Pro Phe Arg Lys Asn Glu Met Lys Glu Gln
    450                 455                 460

Glu Asn Ser Lys Ile Ser His Lys Thr Tyr Leu Val Lys Lys Ser Asn
465                 470                 475                 480
```

-continued

```
Leu Pro Val His Gln Asp Ala Ser Glu Gly Glu Ala Pro Val Gln Asp
            485                 490                 495

Ile Glu Lys Asp Leu Lys Gln Met Arg Leu Gln Asn Thr Lys Glu Ser
        500                 505                 510

Lys Asn Pro Glu Gln Lys Tyr Lys Ala Lys Lys Gly Val Lys Phe Glu
    515                 520                 525

Ile Asn Leu Asp Lys Cys Ile Ser Asp Glu Asn Ile Leu Gln Glu Glu
530                 535                 540

Glu Ala Met Asp Ile Pro Asn Glu Thr Leu Thr Phe Glu Asp Gly Met
545                 550                 555                 560

Lys Phe Lys Glu Tyr Glu Cys Val Lys Glu His Gly Asp Tyr Thr Asp
                565                 570                 575

Lys Ala Phe Glu Lys Leu His Cys Pro Glu Ala Gly Phe Ser Thr Gln
            580                 585                 590

Thr Val Ala Ala Val Gly Asn Arg Arg Gln Trp Asp Gly Gly Ala Pro
        595                 600                 605

Gln Thr Leu Leu Gln Met Met Ala Val Ala Asp Ile Thr Ser Thr Cys
    610                 615                 620

Pro Thr Gly Pro Asp Ser Glu Ser Val Leu Ser Val Ser Arg Gln Glu
625                 630                 635                 640

Gly Lys Thr Lys Asp Pro Tyr Ser Pro Val Leu Ile Leu Met
                645                 650
```

```
<210> SEQ ID NO 5
<211> LENGTH: 2240
<212> TYPE: DNA
<213> ORGANISM: homo sapiens

<400> SEQUENCE: 5
ctgtctcatt tcagttatct gtggccacaa ggaaagttat ttgtctctgt cttggcaagg      60
ctgggaggaa agttttagct aagaacctca gcccattgga gaccatggat aagtacgatg     120
tgattaaggc catcgggcaa ggtgccttcg ggaaagcata cttagctaaa gggaaatcag     180
atagcaagca ctgtgtcata aaagagatca attttgaaaa gatgcccata caagaaaaag     240
aagcttcaaa gaagaagtg attcttctgg aaaagatgaa acatcccaac attgtagcct     300
tcttcaattc atttcaagag aatggcaggc tgtttattgt aatggaatat tgtgatggag     360
gggatctcat gaaaaggatc aatagacaac ggggtgtgtt atttagtgaa gatcagatcc     420
tcggttggtt tgtacagatt ctctctaggac taaaacatat tcatgacagg aagatattac     480
acagggacat aaaagctcag aacattttc ttagcaagaa cggaatggtg caaagcttg     540 gggactttgg tatagcaaga gtcctgaata attccatgga acttgctcga acttgtattg     600
aacaccttta ctacctgtcc ccagagatct gtcagaataa accctacaac aataaaacgg     660
atatttggtc tcttggctgt gtcttatatg agctctgcac acttaaacat ccttttgagg     720
gtaacaactt acagcagctg gttctgaaga tttgtcaagc acattttgcc ccaatatctc     780
cggggttttc tcgtgagctc cattccttga tatctcagct cttttcaagta tctcctcgag     840 accgaccatc cataaattcc attttgaaaa ggcccttttt agagaatctt attcccaaat     900
atttgactcc tgaggtcatt caggaagaat tcagtcacat gcttatatgc agagcaggag     960
cgccagcttc tcgacatgct gggaaggtgg tccagaagtg taaaatacaa aaagtgagat    1020
tccagggaaa gtgcccacca agatcaagga tatctgtgcc aattaaaagg aatgctatat    1080
tgcatagaaa tgaatggaga ccaccagctg gagcccagaa ggccagatct ataaaaatga    1140
```

```
tagaaagacc caaaattgct gctgtctgtg gacattatga ttattattat gctcaacttg   1200
atatgctgag gaggagagcc cacaaaccaa gttatcaccc tattcctcaa gaaaatactg   1260
gagttgagga ttacggtcag gaaacgaggc atggtccatc cccaagtcaa tggcctgctg   1320
agtaccttca gagaaaattt gaagctcaac aatataagtt gaaagtggag aagcaattgg   1380
gtcttcgtcc atcttctgcc gagccaaatt acaaccagag acaagagcta agaagtaatg   1440
gagaagagcc tagattccag gagctgccat ttaggaaaaa cgaaatgaag gaacaggaat   1500
attggaagca gttagaggaa atacgccaac agtaccacaa tgacatgaaa gaaattagaa   1560
agaagatggg gagagaacca gaggagaact caaaaataag tcataaaacc tatttggtga   1620
agaagagtaa cctgcctgtc catcaagatg catctgaggg agaagcacct gtgcaggaca   1680
ttgaaaaaga cttgaaacaa atgaggcttc agaacacaaa ggaaagtaaa aatccagaac   1740
agaaatataa agctaagaag ggggtaaaat ttgaaattaa tttagacaaa tgtatttctg   1800
atgaaaacat cctccaagag gaagaggcaa tggatatacc aaatgaaact ttgacctttg   1860
aggatggcat gaagtttaag gaatatgaat gtgtaaagga gcatggagat tatacagaca   1920
aagcatttga aaaacttcac tgcccagaag cagggttttc cacgcagact gtagctgctg   1980
tgggaaacag gaggcagtgg gatggaggag cgcctcagac tctgctgcag atgatggcag   2040
tggccgacat cacctccacc tgccccacgg ggcctgacga tgagtctgtg cttagcgtca   2100
gtcgtcagga agggaagacc aaggacccgt acagcccagt gctcatcctg atgtgatagt   2160
ctacttctca ctatacaccc tatagatctt gtatcagaca ctttcaaata tgttgttttg   2220
atatctccct ataccaaaaa                                                2240

<210> SEQ ID NO 6
<211> LENGTH: 1167
<212> TYPE: DNA
<213> ORGANISM: homo sapiens

<400> SEQUENCE: 6
atgttaaaag tgaagaggct ggaagaattc aacacgtgtt ataacagcaa ccagctggag     60
aaaatggcct tttttcagtg cagggaagag gtggagaaag tgaagtgttt tctggaaaaa    120
aattctgggg accaggattc aagatctgga cataatgagg cgaaggaggt gtggtcaaac    180
gccgacctga cggaaaggat gcccgtcaaa agcaaaagga catcagccct cgcagttgac    240
atcccggctc ctccggcccc atttgatcat cgtattgtga cagccaagca aggagcggtc    300
aacagcttct atactgtgag caagacagaa atcctaggag gagggcgttt cggccaggtt    360
cacaagtgtg aggagacggc cacaggtctg aagctggcag ccaaaatcat caagaccaga    420
ggcatgaagg acaaggagga ggtgaagaac gagatcagcg tcatgaacca gctggaccac    480
gcgaacctca tccagctgta cgatgccttc gagtctaaga cgacattgt cctggtcatg    540 gagtatgtgg atggtgggga gctgtttgac cgcatcatcg atgagagcta caatttgacg    600
gagcttgata ccatcctgtt catgaagcag atatgtgagg ggataaggca catgcatcag    660
atgtacattc tccacttgga cctgaagcct gagaatatcc tgtgtgtgaa tcgggatgct    720
aagcaaataa aaattattga ttttggattg gccagaagat acaaaccag agagaagctg    780 aaggtgaact ttggaacccc agaatttctc gcccctgaag ttgtgaacta tgattttgtt    840
tcatttccca ctgacatgtg gagtgtgggg gtcatcgcct atatgctact agcggttgg     900 tcgcctttcc tgggtgacaa tgatgctgag acgctgaaca acatcctggc ctgcaggtgg    960
gacttagagg atgaagaatt tcaggacatc tcggaggagg ccaaggagtt catctctaag   1020
```

-continued

```
cttctgatta aggagaagag ttggcgaata agtgcaagcg aagctctcaa gcacccctgg      1080
ttgtcagacc acaagctcca ctccagactc aatgcccaga agaagaagaa tcgtggctct      1140
gatgcccagg actttgtgac caaatag                                          1167
```

<210> SEQ ID NO 7
<211> LENGTH: 388
<212> TYPE: PRT
<213> ORGANISM: homo sapiens

<400> SEQUENCE: 7

```
Met Leu Lys Val Lys Arg Leu Glu Glu Phe Asn Thr Cys Tyr Asn Ser
 1               5                  10                  15

Asn Gln Leu Glu Lys Met Ala Phe Phe Gln Cys Arg Glu Glu Val Glu
             20                  25                  30

Lys Val Lys Cys Phe Leu Glu Lys Asn Ser Gly Asp Gln Asp Ser Arg
         35                  40                  45

Ser Gly His Asn Glu Ala Lys Glu Val Trp Ser Asn Ala Asp Leu Thr
     50                  55                  60

Glu Arg Met Pro Val Lys Ser Lys Arg Thr Ser Ala Leu Ala Val Asp
 65                  70                  75                  80

Ile Pro Ala Pro Pro Ala Pro Phe Asp His Arg Ile Val Thr Ala Lys
                 85                  90                  95

Gln Gly Ala Val Asn Ser Phe Tyr Thr Val Ser Lys Thr Glu Ile Leu
            100                 105                 110

Gly Gly Gly Arg Phe Gly Gln Val His Lys Cys Glu Gly Thr Ala Thr
        115                 120                 125

Gly Leu Lys Leu Ala Ala Lys Ile Ile Lys Thr Arg Gly Met Lys Asp
    130                 135                 140

Lys Glu Glu Val Lys Asn Glu Ile Ser Val Met Asn Gln Leu Asp His
145                 150                 155                 160

Ala Asn Leu Ile Gln Leu Tyr Asp Ala Phe Glu Ser Lys Asn Asp Ile
                165                 170                 175

Val Leu Val Met Glu Tyr Val Asp Gly Gly Glu Leu Phe Asp Arg Ile
            180                 185                 190

Ile Asp Glu Ser Tyr Asn Leu Thr Glu Leu Asp Thr Ile Leu Phe Met
        195                 200                 205

Lys Gln Ile Cys Glu Gly Ile Arg His Met His Gln Met Tyr Ile Leu
    210                 215                 220

His Leu Asp Leu Lys Pro Glu Asn Ile Leu Cys Val Asn Arg Asp Ala
225                 230                 235                 240

Lys Gln Ile Lys Ile Ile Asp Phe Gly Leu Ala Arg Arg Tyr Lys Pro
                245                 250                 255

Arg Glu Lys Leu Lys Val Asn Phe Gly Thr Pro Glu Phe Leu Ala Pro
            260                 265                 270

Glu Val Val Asn Tyr Asp Phe Val Ser Phe Pro Thr Asp Met Trp Ser
        275                 280                 285

Val Gly Val Ile Ala Tyr Met Leu Leu Ser Gly Leu Ser Pro Phe Leu
    290                 295                 300

Gly Asp Asn Asp Ala Glu Thr Leu Asn Asn Ile Leu Ala Cys Arg Trp
305                 310                 315                 320

Asp Leu Glu Asp Glu Glu Phe Gln Asp Ile Ser Glu Glu Ala Lys Glu
                325                 330                 335

Phe Ile Ser Lys Leu Leu Ile Lys Glu Lys Ser Trp Arg Ile Ser Ala
            340                 345                 350
```

Ser Glu Ala Leu Lys His Pro Trp Leu Ser Asp His Lys Leu His Ser
        355                 360                 365

Arg Leu Asn Ala Gln Lys Lys Asn Arg Gly Ser Asp Ala Gln Asp
    370                 375                 380

Phe Val Thr Lys
385

<210> SEQ ID NO 8
<211> LENGTH: 1197
<212> TYPE: DNA
<213> ORGANISM: homo sapiens

<400> SEQUENCE: 8

| | | | | | |
|---|---|---|---|---|---|
| atgttaaaag | tgaagaggct | ggaagaattc | aacacgtgtt | ataacagcaa | ccagctggag | 60 |
| aaaatggcct | tttttcagtg | cagggaagag | gtggagaaag | tgaagtgttt | tctggaaaaa | 120 |
| aattctgggg | accaggattc | aagatctgga | cataatgagg | cgaaggaggt | gtggtcaaac | 180 |
| gccgacctga | cggaaaggat | gcccgtcaaa | agcaaaagga | catcagccct | cgcagttgac | 240 |
| atcccggctc | ctccggcccc | atttgatcat | cgtattgtga | cagccaagca | aggagcggtc | 300 |
| aacagcttct | atactgtgag | caagacagaa | atcctaggag | gagggcgttt | cggccaggtt | 360 |
| cacaagtgtg | aggagacggc | cacaggtctg | aagctggcag | ccaaaatcat | caagaccaga | 420 |
| ggcatgaagg | acaaggagga | ggtgaagaac | gagatcagcg | tcatgaacca | gctggaccac | 480 |
| gcgaacctca | tccagctgta | cgatgccttc | gagtctaaga | cgacattgt | cctggtcatg | 540 |
| gagtatgtgg | atggtgggga | gctgtttgac | cgcatcatcg | atgagagcta | caattttgacg | 600 |
| gagcttgata | ccatcctgtt | catgaagcag | atatgtgagg | ggataaggca | catgcatcag | 660 |
| atgtacattc | tccacttgga | cctgaagcct | gagaatatcc | tgtgtgtgaa | tcgggatgct | 720 |
| aagcaaataa | aaattattga | ttttggattg | gccagaagat | acaaacccag | agagaagctg | 780 |
| aaggtgaact | ttggaacccc | agaatttctc | gcccctgaag | ttgtgaacta | tgattttgtt | 840 |
| tcatttccca | ctgacatgtg | gagtgtgggg | gtcatcgcct | atatgctact | tagcggtttg | 900 |
| tcgcctttcc | tgggtgacaa | tgatgctgag | acgctgaaca | catcctggc | ctgcaggtgg | 960 |
| gacttagagg | atgaagaatt | tcaggacatc | tcggaggagg | ccaaggagtt | catctctaag | 1020 |
| cttctgatta | aggagaagag | ttggcgaata | agtgcaagcg | aagctctcaa | gcaccctgg | 1080 |
| ttgtcagacc | acaagctcca | ctccagactc | aatgcccagg | tgaccacggc | ttcttgctct | 1140 |
| tcctctttt | ctcctgtctg | cctgtctttt | gaagatcaga | tgctggagtc | atcttaa | 1197 |

<210> SEQ ID NO 9
<211> LENGTH: 398
<212> TYPE: PRT
<213> ORGANISM: homo sapiens

<400> SEQUENCE: 9

Met Leu Lys Val Lys Arg Leu Glu Glu Phe Asn Thr Cys Tyr Asn Ser
 1               5                  10                  15

Asn Gln Leu Glu Lys Met Ala Phe Phe Gln Cys Arg Glu Glu Val Glu
                20                  25                  30

Lys Val Lys Cys Phe Leu Glu Lys Asn Ser Gly Asp Gln Asp Ser Arg
            35                  40                  45

Ser Gly His Asn Glu Ala Lys Glu Val Trp Ser Asn Ala Asp Leu Thr
        50                  55                  60

Glu Arg Met Pro Val Lys Ser Lys Arg Thr Ser Ala Leu Ala Val Asp
65                  70                  75                  80

-continued

```
Ile Pro Ala Pro Pro Ala Pro Phe Asp His Arg Ile Val Thr Ala Lys
            85                  90                  95
Gln Gly Ala Val Asn Ser Phe Tyr Thr Val Ser Lys Thr Glu Ile Leu
            100                 105                 110
Gly Gly Gly Arg Phe Gly Gln Val His Lys Cys Glu Glu Thr Ala Thr
            115                 120                 125
Gly Leu Lys Leu Ala Ala Lys Ile Ile Lys Thr Arg Gly Met Lys Asp
        130                 135                 140
Lys Glu Glu Val Lys Asn Glu Ile Ser Val Met Asn Gln Leu Asp His
145                 150                 155                 160
Ala Asn Leu Ile Gln Leu Tyr Asp Ala Phe Glu Ser Lys Asn Asp Ile
                165                 170                 175
Val Leu Val Met Glu Tyr Val Asp Gly Gly Glu Leu Phe Asp Arg Ile
                180                 185                 190
Ile Asp Glu Ser Tyr Asn Leu Thr Glu Leu Asp Thr Ile Leu Phe Met
            195                 200                 205
Lys Gln Ile Cys Glu Gly Ile Arg His Met His Gln Met Tyr Ile Leu
210                 215                 220
His Leu Asp Leu Lys Pro Glu Asn Ile Leu Cys Val Asn Arg Asp Ala
225                 230                 235                 240
Lys Gln Ile Lys Ile Ile Asp Phe Gly Leu Ala Arg Arg Tyr Lys Pro
                245                 250                 255
Arg Glu Lys Leu Lys Val Asn Phe Gly Thr Pro Glu Phe Leu Ala Pro
                260                 265                 270
Glu Val Val Asn Tyr Asp Phe Val Ser Phe Pro Thr Asp Met Trp Ser
            275                 280                 285
Val Gly Val Ile Ala Tyr Met Leu Leu Ser Gly Leu Ser Pro Phe Leu
        290                 295                 300
Gly Asp Asn Asp Ala Glu Thr Leu Asn Asn Ile Leu Ala Cys Arg Trp
305                 310                 315                 320
Asp Leu Glu Asp Glu Glu Phe Gln Asp Ile Ser Glu Glu Ala Lys Glu
                325                 330                 335
Phe Ile Ser Lys Leu Leu Ile Lys Glu Lys Ser Trp Arg Ile Ser Ala
                340                 345                 350
Ser Glu Ala Leu Lys His Pro Trp Leu Ser Asp His Lys Leu His Ser
            355                 360                 365
Arg Leu Asn Ala Gln Val Thr Thr Ala Ser Cys Ser Ser Ser Phe Ser
        370                 375                 380
Pro Val Cys Leu Ser Phe Glu Asp Gln Met Leu Glu Ser Ser
385                 390                 395
```

<210> SEQ ID NO 10
<211> LENGTH: 1744
<212> TYPE: DNA
<213> ORGANISM: homo sapiens

<400> SEQUENCE: 10

```
ctctcgtagt ggacacttgt cttttcagaa gatttatacg actgagagtc aaaactttta    60
ccagagactt tcatagtcag tttgaattct gcaaaatttc tctttatctt ctggaatgta   120
tgctctagac ttggagtggc tcaagctctt cgatgtgatc ctatcaatgt caagagaaag   180
aagcactgaa gagtcataat tgtgtcctga tttataaatc ggagacagag ggagacgaaa   240
accacactcc agaaagtagc ttaatcggac tcactactaa gatgttaaaa gtgaagaggc   300
tggaagaatt caacacgtgt tataacagca accagctgga gaaaatggcc ttttttcagt   360
```

-continued

```
gcagggaaga ggtggagaaa gtgaagtgtt ttctggaaaa aaattctggg gaccaggatt      420
caagatctgg acataatgag gcgaaggagg tgtggtcaaa cgccgacctg acggaaagga      480
tgcccgtcaa aagcaaaagg acatcagccc tcgcagttga catcccggct cctccggccc      540
catttgatca tcgtattgtg acagccaagc aaggagcggt caacagcttc tatactgtga      600
gcaagacaga aatcctagga ggagggcgtt tcggccaggt tcacaagtgt gaggagacgg      660
ccacaggtct gaagctggca gccaaaatca tcaagaccag aggcatgaag gacaaggagg      720
aggtgaagaa cgagatcagc gtcatgaacc agctggacca cgcgaacctc atccagctgt      780
acgatgcctt cgagtctaag aacgacattg tcctggtcat ggagtatgtg gatggtgggg      840
agctgtttga ccgcatcatc gatgagagct acaatttgac ggagcttgat accatcctgt      900
tcatgaagca gatatgtgag gggataaggc acatgcatca gatgtacatt ctccacttgg      960
acctgaagcc tgagaatatc ctgtgtgtga atcgggatgc taagcaaata aaaattattg     1020
attttggatt ggccagaaga tacaaaccca gagagaagct gaaggtgaac tttggaaccc     1080
cagaatttct cgcccctgaa gttgtgaact atgattttgt ttcatttccc actgacatgt     1140
ggagtgtggg ggtcatcgcc tatatgctac ttagcggttt gtcgcctttc ctgggtgaca     1200
atgatgctga gacgctgaac aacatcctgg cctgcaggtg ggacttagag gatgaagaat     1260
ttcaggacat ctcggaggag gccaaggagt tcatctctaa gcttctgatt aaggagaaga     1320
gttggcgaat aagtgcaagc gaagctctca agcacccctg gttgtcagac cacaagctcc     1380
actccagact caatgcccag aagaagaaga atcgtggctc tgatgcccag gactttgtga     1440
ccaaatagtc tacaggaggc agccatttgg aaggaaaact gctgtggttg ctgctgcttc     1500
gagaaaattt tttgaaaaat cagcagttct gatgccttga cccctgtgat gacctggtag     1560
tcttagcagg gggagccctc gaccctgaat gtgaacttga actggagtgc ctctgctgcg     1620
ctcagaggaa cacccagcgc tgcggtctgg tctcagggcg caaacacatc cctgcacccg     1680
gtggtggtga tgttgggaag atgtttccct gccatctttg agattttta cttttttaaa     1740 aaaa                                                                 1744
```

HUMAN KINASE PROTEINS AND POLYNUCLEOTIDES ENCODING THE SAME

The present application claims the benefit of U.S. Provisional Application No. 60/229,280 which was filed on Aug. 31, 2000 and is herein incorporated by reference in its entirety.

1. INTRODUCTION

The present invention relates to the discovery, identification, and characterization of novel human polynucleotides encoding proteins that share sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to, NIMA (never in mitosis A) related kinases, serine-threonine kinases, calcium/calmodulin-dependent kinases, and myosin light chain kinases. Accordingly, the described NHPs encode novel kinases having homologues and orthologs across a range of phyla and species.

The novel human polynucleotides described herein, encode open reading frames (ORFs) encoding proteins of 683, 654, 388, and 398 amino acids in length (see respectively SEQ ID NOS: 2, 4, 7 and 9).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–10 are "knocked-out" they provide a method of identifying phenotypic expression of the particular gene as well as a method of assigning function to previously unknown genes. In addition, animals in which the unique NHP sequences described in SEQ ID NOS:1–10 are "knocked-out" provide a unique source in which to elicit antibodies to homologous and orthologous proteins which would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–10 are useful for the identification of protein coding sequence and mapping a unique gene to a particular chromosome. These sequences identify actual, biologically relevant, exon splice junctions as opposed to those that might have been predicted bioinformatically from genomic sequence alone.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins. SEQ ID NOS:5 and 10 describe NHP ORFs and flanking sequences.

5. DETAILED DESCRIPTION OF THE INVENTION

The NHPs, described for the first time herein, are novel proteins that are expressed in, inter alia, human cell lines and human fetal brain, brain, pituitary, cerebellum, spinal cord, thymus, spleen, lymph node, bone marrow, trachea, lung, kidney, fetal liver, liver, prostate, testis, thyroid, small intestine, heart, uterus, placenta, mammary gland, adipose, esophagus, cervix, rectum, fetal kidney, and fetal lung (SEQ ID NOS:2 and 4), or human pituitary, kidney, thyroid, skeletal muscle, and heart cells (SEQ ID NOS: 7 and 9). The described sequences were compiled from sequences available in GENBANK, and cDNAs generated from kidney, testis, trachea, esophagus, pituitary, human gene trapped products (SEQ ID NOS: 2 and 4), or bone marrow and skeletal muscle mRNAs (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/ self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., NY, at p. 2.10.3) and encodes a functionally equivalent expression product. Additionally, contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. Nos. 5,837,458 or 5,723,323 both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–10 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–10, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–10 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–10.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–10 provides detailed information about transcriptional changes involved in a specific pathway, potentially leading to the identification of novel components or gene functions that manifest themselves as novel phenotypes.

Probes consisting of sequences first disclosed in SEQ ID NOS:1–10 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–10 can be utilized in microarrays or other assay formats, to screen collections of genetic material from patients who have a particular medical condition. These investigations can also be carried out using the sequences first disclosed in SEQ ID NOS:1–10 in silico and by comparing previously collected genetic databases and the disclosed sequences using computer software known to those in the art.

Thus the sequences first disclosed in SEQ ID NOS:1–10 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–10. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP nucleic acid sequences). With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, N.Y.; and Ausubel et al., 1989, Current Protocols in Molecular Biology, Green Publishing Associates and Wiley Interscience, NY).

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, and 5,723,323 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and corresponding deduced amino acid sequences of the described NHPs are presented in the Sequence Listing.

Expression analysis has provided evidence that the described NHPs can be expressed in a broad range of human tissues (SEQ ID NOS: 2 and 4), or a relatively narrow range of human tissues (SEQ ID NOS: 7 and 9). In addition to serine-threonine kinases, the described NHPs also share significant similarity to a range of additional kinase families, including kinases associated with signal transduction, from a variety of phyla and species. The exons encoding SEQ ID NOS: 2 and 4 is apparently encoded on human chromosome 6 (see GENBANK accession no. AL138876) and the exons encoding SEQ ID NOS: 7 and 9 is apparently encoded on human chromosome 13 (see GENBANK accession no. AL139082). Accordingly, the described sequences are additionally useful for mapping the coding regions of human genomic sequence and for identifying and biologically validating exon splice junctions.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP expression products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP sequences may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS AND NHP POLYPEPTIDES

NHP products, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to the NHP, as reagents in assays for screening for compounds that can be used as pharmaceutical reagents useful in the therapeutic treatment of mental, biological, or medical disorders and disease.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences which indicates that they may be cytoplasmic or possibly nuclear proteins, although they may also be secreted or membrane associated.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4–1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of nonoccluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes, which can be employed in tk−, hgprt− or aprt− cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New, R. R. C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111,701 and 60/056,713, both of which are herein incorporated by reference, for examples of such transducing sequences) to facilitate passage across cellular membranes and can optionally be engineered to include nuclear localization.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (see U.S. Pat. Nos. 6,075,181, 5,877,397 and 6,150,584, which are herein incorporated by reference in their entirety).

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence that:
   (a) encodes the amino acid sequence shown in SEQ ID NO:2; and
   (b) hybridizes under stringent conditions to the nucleotide sequence of SEQ ID NO:1 or the complement thereof.

2. An isolated nucleic acid molecule comprising a nucleotide sequence encoding the amino acid sequence shown in SEQ ID NO:2.

3. The isolated nucleic acid molecule of claim 2, wherein said nucleic acid molecule has the sequence of SEQ ID NO:1.

4. An expression vector comprising a nucleotide sequence that encodes the amino acid sequence shown in SEQ ID NO:2.

5. The expression vector of claim 4 wherein said nucleic acid sequence is that of SEQ ID NO:1.

6. A host cell comprising tlie expression vector of claim 4.

7. The host cell of claim 6 wherein said nucleic acid sequence is that of SEQ ID NO:1.

* * * * *